(12) United States Patent
Maixner et al.

(10) Patent No.: US 7,385,073 B2
(45) Date of Patent: *Jun. 10, 2008

(54) METHOD FOR REDUCING THE CONTENT OF AN UNSATURATED AMINE IN A MIXTURE CONTAINING AN AMINO NITRILE, A DIAMINE, A DINITRILE OR MIXTURES THEREOF

(75) Inventors: Stefan Maixner, Schwetzingen (DE); Christoph Benisch, Mannheim (DE); Hermann Luyken, Ludwigshafen (DE); Peter Baβler, Viernheim (DE); Rolf-Hartmuth Fischer, Heidelberg (DE); Johann-Peter Melder, Böhl-Iggelheim (DE); Andreas Ansmann, Wiesloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 344 days.

This patent is subject to a terminal disclaimer.

(21) Appl. No.: 10/515,281

(22) PCT Filed: May 21, 2003

(86) PCT No.: PCT/EP03/05313

§ 371 (c)(1),
(2), (4) Date: Nov. 22, 2004

(87) PCT Pub. No.: WO03/099768

PCT Pub. Date: Dec. 4, 2003

(65) Prior Publication Data

US 2005/0222449 A1 Oct. 6, 2005

(30) Foreign Application Priority Data

May 28, 2002 (DE) .............................. 102 23 827

(51) Int. Cl.
*C07C 253/34* (2006.01)
(52) U.S. Cl. ..................................... 558/452; 564/498
(58) Field of Classification Search .................... None
See application file for complete search history.

(56) References Cited

U.S. PATENT DOCUMENTS

| 2,762,835 | A |   | 9/1956  | Swerdloff |              |
|-----------|---|---|---------|-----------|--------------|
| 2,890,567 | A | * | 6/1959  | Taylor et al. | .................. 57/239 |
| 3,696,153 | A |   | 10/1972 | Kershaw et al. |          |
| 4,601,859 | A |   | 7/1986  | Galle et al. |           |
| 5,961,788 | A | * | 10/1999 | Ostermaier | .................. 203/37 |
| 6,147,208 | A |   | 11/2000 | Achhammer et al. | ....... 540/538 |
| 6,169,199 | B1 |  | 1/2001  | Rehfinger et al. |      |
| 6,252,115 | B1 |  | 6/2001  | Luyken et al. |        |
| 6,359,178 | B1 | * | 3/2002  | Fischer et al. | .............. 564/492 |
| 6,472,501 | B1 | * | 10/2002 | Fergusson et al. | .......... 528/310 |
| 6,479,658 | B1 | * | 11/2002 | Brunelle et al. | ............. 540/485 |
| 6,548,166 | B2 | * | 4/2003  | Figuly et al. | ................ 428/370 |
| 6,828,457 | B2 | * | 12/2004 | Ohlbach et al. | ............ 558/452 |

FOREIGN PATENT DOCUMENTS

| DE | 848 654    | 9/1952  |
|----|------------|---------|
| DE | 954 416    | 12/1956 |
| DE | 42 35 466  | 4/1994  |
| DE | 195 00 222 | 7/1996  |
| DE | 185 48 489 | 6/1997  |
| EP | 497 333    | 8/1992  |

(Continued)

OTHER PUBLICATIONS

Ziemecki, S.B.; Studies in Surface Science and Catalysis (1993), abstract.*

(Continued)

*Primary Examiner*—Rebecca Anderson
*Assistant Examiner*—Sun Jae Y Loewe
(74) *Attorney, Agent, or Firm*—Novak Druce + Quigg LLP

(57) ABSTRACT

A process for reducing the level of an aliphatic monounsaturated amine (IV) in a mixture (V) containing an aminonitrile (I) or a diamine (II) or a dinitrile (III) or mixtures thereof as well as said mine (IV) by a) reacting said mixture (V) with an anionic nucleophile (VI) which contains a nucleophilic atom selected from the group consisting of oxygen, nitrogen and sulfur, which is capable of taking up an H⁺ ion to form an acid having a $pK_a$ value in the range from 7 to 11, as measured in water at 25° C., and which has a relative nucleophilicity, as measured in methyl perchlorate/methanol at 25° C., in the range from 3.4 to 4.7 when said nucleophilic atom is oxygen, in the range from 4.5 to 5.8 when said nucleophilic atom is nitrogen, and in the range from 5.5 to 6.8 when said nucleophilic atom is sulfur, in an amount in the range from 0.01 to 10 mol per mole of said amine (IV) in said mixture (V) at a temperature in the range from 50 to 200° C. to obtain a mixture (VII), b) distilling said aminonitrile (I) or said diamine (II) or said dinitrile (III) or mixtures thereof from said mixture (VII) at a temperature in the range from 50 to 200° C. and at a pressure in the range from 0.1 to 100 kPa to obtain a bottom product (VIII), which comprises c) distilling an aminonitrile (I) or diamine (II) or dinitrile (III) or mixtures thereof from said bottom product (VIII) at a temperature which is lower than that chosen in step b).

22 Claims, No Drawings

FOREIGN PATENT DOCUMENTS

| | | |
|---|---|---|
| EP | 0 502 439 | 9/1992 |
| WO | 92/21650 | 12/1992 |
| WO | 93/14064 | 7/1993 |
| WO | 93/16984 | 9/1993 |
| WO | WO 98/34900 | 8/1998 |
| WO | WO 98/34912 | 8/1998 |
| WO | 02/44135 | 6/2002 |

OTHER PUBLICATIONS

Marchildon, et al. WO2000024808, May 4, 2000, abstract.*

XP-001064740, Nucleophilic Reactivity, Koskikallio, Acta Chemica Scandinavica 23 (1969) 1477-1489.

Achhammer et al., esp@cenet English language Abstract of document (AB).

Immel et al., esp@cenet English language Abstract of document (AC).

Weissermel et al., "*Industrielle Organische Chemie*," (Industrial organic chemistry), VCH Verlags-gesellschaft mbH, $3^{rd}$ Ed., Weinheim, 1988, p. 266.

* cited by examiner

METHOD FOR REDUCING THE CONTENT OF AN UNSATURATED AMINE IN A MIXTURE CONTAINING AN AMINO NITRILE, A DIAMINE, A DINITRILE OR MIXTURES THEREOF

The present invention relates to a process for reducing the level of an aliphatic monounsaturated amine (IV) in a mixture (V) containing an aminonitrile (I) or a diamine (II) or a dinitrile (III) or mixtures thereof as well as said amine (IV) by a) reacting said mixture (V) with an anionic nucleophile (VI)
   which contains a nucleophilic atom selected from the group consisting of
   oxygen, nitrogen and sulfur,
   which is capable of taking up an $H^+$ ion to form an acid having a $pK_a$ value in the range from 7 to 11, as measured in water at 25° C., and
   which has a relative nucleophilicity, as measured in methyl perchlorate/methanol at 25° C., in the range from 3.4 to 4.7 when said nucleophilic atom is oxygen, in the range from 4.5 to 5.8 when said nucleophilic atom is nitrogen, and
   in the range from 5.5 to 6.8 when said nucleophilic atom is sulfur,
   in an amount in the range from 0.01 to 10 mol per mole of said amine (IV) in said mixture (V) at a temperature in the range from 50 to 200° C. to obtain a mixture (VII), b) distilling said aminonitrile (I) or said diamine (II) or said dinitrile (III) or mixtures thereof from said mixture (VII) at a temperature in the range from 50 to 200° C. and at a pressure in the range from 0.1 to 100 kPa to obtain a bottom product (VIII),
   which comprises c) distilling an aminonitrile (I) or diamine (II) or dinitrile (III) or mixtures thereof from said bottom product (VIII) at a temperature which is lower than that chosen in step b).

Mixtures containing an aminonitrile, a diamine, a dinitrile or mixtures thereof as well as an unsaturated amine (for the purposes of the present invention an unsaturated amine being a cyclic or linear compound containing at least one carbon-nitrogen double bond or a compound capable of forming at least one carbon-nitrogen double bond, for example by an elimination reaction) are customarily obtained in the partial hydrogenation of dinitriles to aminonitriles or to a mixture of aminonitriles and diamines or in the full hydrogenation of dinitriles to diamines.

The partial hydrogenation of adiponitrile (ADN) to coproduce hexamethylenediamine (HMD) and 6-aminocapronitrile (ACN) and also the full hydrogenation of ADN to HMD in the presence of a catalyst based on a metal such as nickel, cobalt, iron, rhodium or ruthenium is generally known, for example from: K. Weissermel, H.-J. Arpe, Industrielle Organische Chemie, 3rd edition, VCH Verlagsgesellschaft mbH, Weinheim, 1988, page 266, U.S. Pat. Nos. 4,601,859, 2,762, 835, 2,208,598, DE-A 848 654, DE-A 954 416, DE-A 42 35 466, U.S. Pat. No. 3,696,153, DE-A 19500222, WO-A-92/21650 and DE-A-19548289.

By-products include azepine derivatives such as N-(2-azepano)-1,6-diaminohexane and N-(2-azepano)-6-aminocapronitrile, especially 2-aminoazepan and tetrahydroazepine (THA).

These azepine derivatives, which on account of their coloring effect and their adverse effect on product properties constitute undesirable impurities in the aminonitriles and diamines customarily used for the manufacture of fibers or engineering plastics, are very difficult to separate from the aminonitriles, diamines or mixtures thereof.

EP-A-497333 describes the separation of aliphatic aminonitriles or aliphatic diamines from mixtures containing an aliphatic aminonitrile or aliphatic diamine and a cyclic aliphatic monounsaturated amine by addition of bases in a stoichiometric excess, based on the cyclic aliphatic monounsaturated amine. Bases which are recommended include alkali metal hydroxides, alkaline earth metal hydroxides, tetraalkylammonium hydroxide, alkali metal alkoxides and alkaline earth metal alkoxides.

The disadvantage of this process is a concurrently occurring polymerization of product of value that leads to an appreciable loss of product of value and to undesirable deposits in the vessels and machines used to practice the process.

PCT/EP01/13954, as yet unpublished at the date of the present application, describes reducing the level of an aliphatic monounsaturated amine in a mixture containing an aminonitrile, a diamine or mixtures thereof as well as the aliphatic monounsaturated amine in a process which corresponds to steps a) and b) of the present process. The bottom product obtained in step b) is discarded in the cited process.

It is an object of the present invention to provide a process for reducing the level of an aliphatic monounsaturated amine in a mixture containing an aminonitrile or diamine or mixtures thereof and an aliphatic monounsaturated amine in a technically simple and economical manner with a higher yield of product of value while avoiding the disadvantages mentioned.

We have found that this object is achieved, surprisingly, by the process defined at the beginning in that further aminonitrile (I), diamine (II), dinitrile (III) or mixtures thereof are obtainable by a distillation as per step c) from the bottom product already obtained by distillation in step b).

Useful aminonitriles (I) include compounds having one or more, such as two, three or four, preferably one, nitrile group, especially compounds which have at least one nitrile group adjacent to an aliphatic carbon atom which carries one or two, preferably two, hydrogen atoms, or mixtures thereof.

Useful aminonitriles (I) include compounds having one or more, such as two, three or four, preferably one, amino group, especially compounds which have at least one amino group adjacent to an aliphatic carbon atom which carries one or two, preferably two, hydrogen atoms, or mixtures thereof. Particular preference is given to aminonitriles having a terminal amino group, ie an amino group located at the end of an alkyl chain.

The aminonitrile (I) is preferably based on an alkyl skeleton.

The aminonitrile (I) preferably has from 4 to 12 carbon atoms.

The aminonitrile (I) is preferably selected from the group consisting of 4-aminobutyronitrile, 5-aminovaleronitrile, 2-methyl-5-aminovaleronitrile, 6-aminocapronitrile and 12-aminododecanenitrile, especially 6-aminocapronitrile.

Such aminonitriles may be prepared in a conventional manner.

6-Aminocapronitrile may be obtained by partial catalytic hydrogenation of ADN with a gas containing molecular hydrogen to give mixtures containing HMD and ACN. Catalysts useful in this hydrogenation may preferably be based on a metal selected from the group consisting of ruthenium, rhodium, nickel, cobalt and preferably iron, and the catalysts may contain further elements as promoters. In the case of iron-based catalysts, useful promoters include in particular one or more, such as two, three, four or five, elements selected from the group consisting of aluminum, silicon, zirconium, titanium and vanadium.

Such catalysts and also the process conditions for the reaction mentioned are described for example in WO-A-96/20166, DE-A-19636768 and DE-A-19646436.

Useful diamines (II) include compounds having two or more, such as two, three or four, preferably two, amino groups, especially compounds having at least two amino groups adjacent to an aliphatic carbon atom which carries one or two, preferably two, hydrogen atoms, particularly preferably diamines having terminal amino groups, ie amino groups located at the ends of an alkyl chain, or mixtures thereof.

The diamine (II) is preferably based on an alkyl skeleton.

The diamine (II) preferably has from 4 to 12 carbon atoms.

The diamine (II) is preferably selected from the group consisting of 1,4-diaminobutane, 1,5-diaminopentane, 2-methyl-1,5-diaminopentane, 1,6-diaminohexane (HMD) and 1,12-diaminododecane.

Such diamines may be prepared in a conventional manner.

HMD may be obtained by partial catalytic hydrogenation of ADN with a gas containing molecular hydrogen to give mixtures containing HMD and ACN or by full hydrogenation of ADN with a gas containing molecular hydrogen.

Catalysts useful in this hydrogenation may preferably be based on a metal selected from the group consisting of ruthenium, rhodium, nickel, cobalt and preferably iron, and the catalysts may contain further elements as promoters. In the case of iron-based catalysts, useful promoters include in particular one or more, such as two, three, four or five, elements selected from the group consisting of aluminum, silicon, zirconium, titanium and vanadium.

Such catalysts and also the process conditions for the reactions mentioned may for example be taken from the publications already mentioned above.

Useful dinitriles (III) include compounds having two or more, such as two, three or four, preferably two, nitrile groups, especially compounds having at least two nitrile groups adjacent to an aliphatic carbon atom which carries one or two, preferably two, hydrogen atoms, particularly preferably dinitriles having terminal nitrile groups, ie nitrile groups located at the end of an alkyl chain, or mixtures thereof.

The dinitrile (III) is preferably on an alkyl skeleton.

The dinitrile (III) preferably has from 4 to 12 carbon atoms.

The dinitrile (III) is preferably selected from the group consisting of 1,2-dinitriloethane, 1,3-dinitrilopropane, 1-methyl-1,3-dinitrilopropane, 1,4-dinitrilobutane and 1,10-dinitrilodecane.

Such dinitriles may be prepared in a conventional manner.

For instance, ADN may be prepared by double hydrocyanation of butadiene in the presence of nickel and phosphorus-containing ligands. Examples of useful catalysts and also process conditions for the reactions mentioned may for example be taken from the publications already mentioned above.

Useful amines (IV) include cyclic or linear compounds containing at least one carbon-nitrogen double bond or a compound capable of forming at least one carbon-nitrogen double bond, for example by an elimination reaction, or mixtures thereof.

The amine (IV) is in particular a compound of formula $R^1-(CH_2)_n-CH=N-(CH_2)_m-R^2$ where n and m are independently 1, 2, 3, 4, 5, 6, 7, 8, 9, 10, 11 or 12 preferably 4, 5 or 6, and $R^1$ and $R^2$ are independently —CN or —NH$_2$, or of the formula

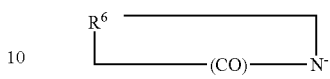

where $R^3$ is an alkenyl radical having 3, 4, 5, 6, 7, 8, 9, 10 or 11 carbon atoms belonging to the ring system.

The amine (IV) is most preferably a compound selected from the group consisting of dihydropyrrole, tetrahydropyridine, 3-methyltetrahydropyridine, tetrahydroazepine, monounsaturated cyclododecylamines or mixtures thereof.

These amines (IV) may be present in the mixture (V) as individual compounds or as adducts, for example with a nitrile (I), especially aminonitrile, in which case these adducts are likewise referred to as an amine (IV) for the purposes of the present invention.

Such amines (IV) and processes for preparing them are generally known.

For instance, tetrahydroazepine may be obtained in partial catalytic hydrogenation of ADN with a gas containing molecular hydrogen to give mixtures containing HMD and ACN, generally in amounts from 1 to 10 000 ppm based on the mixture, by the processes which are described for the preparation of ACN, in mixtures (V).

Similarly, the amines (IV) mentioned may be formed by oxidation of amines such as HMD, for example with gases containing molecular oxygen.

In a preferred embodiment, the mixture (V) may be the reaction effluent obtained from the partial catalytic hydrogenation, such as gas phase hydrogenation or liquid phase hydrogenation, of dinitriles, especially ADN, with a gas containing molecular hydrogen, in the presence of a catalyst such as a suspension catalyst or fixed bed catalyst, said reaction effluent containing ACN as aminonitrile (I), HMD as diamine (II), residual ADN as dinitrile (III) and tetrahydroazepine as amine (IV) in the case where ADN is the starting compound, in which case, if desired, any solvent previously used in the hydrogenation may be partly or wholly separated off. From experience to date, it may be preferable for any catalyst used in the hydrogenation to be separated off before the mixture (V) is used in the process of the present invention.

Advantageously, the mixture containing aminonitrile (I), diamine (II), dinitrile (III) and amine (IV), especially ACN as aminonitrile (I), HMD as diamine (II), residual ADN as dinitrile (III) and tetrahydroazepine as amine (IV) in the case where ADN is the starting compound, may have the diamine (I) removed from it prior to step a) by a conventional process, as by distillation. In this case, the mixture (V) used in step a) can be a mixture containing aminonitrile (I), dinitrile (III) and amine (IV), especially ACN as aminonitrile (I), residual ADN as dinitrile (III) and tetrahydroazepine as amine (IV) in the case where ADN is the starting compound.

Advantageously, the mixture containing aminonitrile (I), diamine (II), dinitrile (III) and amine (IV), especially ACN as aminonitrile (I), HMD as diamine (II), residual ADN as dinitrile (III) and tetrahydroazepine as amine (IV) in the case where ADN is the starting compound, may have the dinitrile (III) removed from it prior to step a) by a conventional process, as by distillation. In this case, the mixture (V) used in step a) can be a mixture containing aminonitrile (I), diamine (II) and amine (IV), especially ACN as aminonitrile (I), HMD as diamine (II) and tetrahydroazepine as amine (IV) in the case where ADN is the starting compound.

Advantageously, the mixture containing aminonitrile (I), diamine (II), dinitrile (III) and amine (IV), especially ACN as aminonitrile (I), HMD as diamine (II), residual ADN as dinitrile (III) and tetrahydroazepine as amine (IV) in the case where ADN is the starting compound, may have the dinitrile (III), and the diamine (I) removed from it prior to step a) by a conventional process, as by distillation. In this case, the mixture (V) used in step a) can be a mixture containing aminonitrile (I) and amine (IV), especially ACN as aminonitrile (I) and tetrahydroazepine as amine (IV) in the case where ADN is the starting compound.

In a preferred embodiment, the mixture (V) may be the reaction effluent obtained from the full catalytic hydrogenation, such as gas phase hydrogenation or liquid phase hydrogenation, of dinitriles, especially ADN, with a gas containing molecular hydrogen, in the presence of a catalyst such as a suspension catalyst or fixed bed catalyst, said reaction effluent containing HMD as diamine (II) and tetrahydroazepine as amine (IV) in the case where ADN is the starting compound, in which case, if desired, any solvent previously used in the hydrogenation may be partly or wholly separated off. From experience to date, it may be preferable for any catalyst used in the hydrogenation to be separated off before the mixture (V) is used in the process of the present invention.

According to the invention, mixture (V) is admixed with an anionic nucleophile (VI).

The term "anionic" means for the purposes of the present invention that the nucleophile (VI) carries one or more, such as two or three, preferably one, net negative charge.

The term "nucleophilic" means for the purposes of the present invention the ability of a compound, as described in Koskikallo, Acta Chem. Scand. 23 (1969) pages 1477-1489, to displace the perchlorate group from methyl perchlorate in methanolic solution at 25° C., the remaining methyl group becoming attached to compound (VI) via a nucleophilic atom of compound (VI).

The nucleophilic atom of compound (VI) may be an atom selected from the group consisting of nitrogen, oxygen and sulfur, preferably nitrogen or oxygen.

According to the invention, compound (VI) is capable of taking up an $H^+$ ion to form an acid having a $pK_a$ value in the range from 7 to 11, and preferably in the range from 8 to 10.5, as measured in water at 25° C.

According to the invention, compound (VI) has a relative nucleophilicity, as measured in methyl perchlorate/methanol at 25° C. as per Koskikallo, Acta Chem. Scand. 23 (1969) pages 1477-1489, and as determined as per pages 1487-1488, in the range from 3.4 to 4.7 and preferably in the range from 3.6 to 4.6 when oxygen is nucleophilic atom, in the range from 4.5 to 5.8 and preferably from 4.8 to 5.7 when nitrogen is the nucleophilic atom and in the range from 5.5 to 6.8 and preferably in the range from 5.8 to 6.7 when sulfur is the nucleophilic atom.

When oxygen is the nucleophilic atom of (VI), phenates can be used with advantage, in which case the aromatic ring system of the phenate may be monosubstituted or polysubstituted, such as disubstituted or trisubstituted, for example by a $C_1$- to $C_4$-alkyl group, such as methyl, ethyl, n-propyl, i-propyl, n-butyl, i-butyl, s-butyl, t-butyl, by halogen, such as fluorine, chlorine, bromine, iodine, by a nitro group, by an ester group, by a carbonyl group or by an amino group.

When nitrogen is the nucleophilic atom of (VI), advantageous compounds contain the structural unit $(R^4R^5N)^-$ where
$R^4$: radical of an organic aliphatic, arylaliphatic or arylic acid, preferably carboxylic acid or sulfonic acid group, and
$R^4$ may be substituted as already described above for phenate, and
$R^5$: radical of an organic aliphatic, arylaliphatic or arylic acid, preferably carboxylic acid or sulfonic acid group, or hydrogen or a $C_1$- to $C_4$-alkyl group, such as methyl, ethyl, n-propyl, i-propyl, n-butyl, i-butyl, s-butyl, t-butyl, and $R^5$ may be substituted as already described above for phenate, and $R^4$ and $R^5$ may be linked together other than by the nitrogen mentioned in the above formula, for example via an alkylene, alkylarylene or arylene bridge, preferably via an arylene bridge.

In a preferred embodiment, the nucleophile (VI) can be a lactam anion of the general formula $$R^6 \overline{\phantom{xx}(CO)\phantom{xx}} N^-$$

where
$R^6$ is an alkylene radical having 3, 4, 5, 6, 7, 8, 9, 10 or 11 carbon atoms belonging to the ring system, and $R^6$ may be substituted as already described above for phenate.

In a preferred embodiment, the nucleophile (VI) can be caprolactam anion.

In a further particularly preferred embodiment, the nucleophile (VI) can be benzenesulfonamide anion.

In a further particularly preferred embodiment, the nucleophile (VI) can be phthalimide anion.

In a further particularly preferred embodiment, the nucleophile (VI) can be phenate.

To balance the negative charge on the anionic nucleophile (VI), the latter can be used together with one or more cations, preferably selected from the group consisting of lithium, sodium, potassium, rubidium, cesium, magnesium and calcium, especially consisting of lithium, sodium, potassium, magnesium and calcium and more preferably consisting of sodium and potassium.

According to the invention, the mixture (V) is admixed with the nucleophile (VI) in an amount in the range from 0.01 to 10 mol per mole of amine (IV) in mixture (V).

Advantageously, the amount of nucleophile (VI) can be at least 0.05 and preferably at least 0.1 mol and especially 0.2 mol per mole of amine (IV) in mixture (V).

Advantageously, the amount of nucleophile (VI) can be at most 1 and especially at most 0.8 and more preferably at most 0.5 mol per mole of amine (VI) in mixture (V).

The nucleophile (VI) can be added to the mixture (V) in a conventional manner, for example in conventional mixing apparatus, such as vessels, product lines and mixing means, to give a mixture (VII).

The nucleophile (VI) can be added to the mixture (V) before the mixture (VII) is introduced into a distillation apparatus for removal as per step b).

Average mean contact times of at least 5 minutes and preferably at least 10 minutes between mixture (V) and nucleophile (VI) prior to addition into a distillation apparatus have been determined to be advantageous.

In general, distinctly longer residence times, such as more than 30 minutes, have been determined to be increasingly advantageous, although appreciably longer residence times become increasingly uneconomical.

From experience to date, average mean contact times between mixture (V) and nucleophile (VI) prior to addition into a distillation apparatus of not more than 360 minutes and preferably not more than 180 minutes and especially not more than 120 minutes have been determined to be advantageous.

Temperatures are advantageously not more than 200° C., preferably not more than 190° C. and especially not more than 180° C.

Temperatures are advantageously at least 50° C., preferably at least 100° C. and especially at least 140° C.

It is similarly possible to introduce mixture (V) and nucleophile (VI) to such an apparatus separately and to conduct the reaction of mixture (V) with nucleophile (VI) and the removal as per step in one process step. Nucleophile (VI) can be added to the distillation apparatus at the top, over the entire height onto one of the separation stages or into the pot.

According to the invention, aminonitrile (I), diamine (II), dinitrile (III) or mixtures thereof are distilled from the mixture (VII) at a pressure of not more than 100 kPa and preferably not more than 10 kPa.

According to the invention, aminonitrile (I), diamine (II), dinitrile (III) or mixtures thereof are distilled from the mixture (VII) at a pressure of not less than 0.1 kPa and preferably not less than 0.5 kPa.

Temperatures are advantageously not more than 200° C., preferably not more than 190° C. and especially not more than 180° C.

Temperatures are advantageously at least 50° C., preferably at least 100° C. and especially at least 140° C.

The distillation may be carried out in customary apparatus as described for example in Kirk-Othmer, Encyclopedia of Chemical Technology, 3rd Ed., Vol. 7, John Wiley & Sons, New York, 1979, pages 870-881, preferably in Ullmann's Encyclopedia of Industrial Chemistry, 5th Ed., Vol. A25, VCH Verlagsgesellschaft mbH, Weinheim, p. 215-226, especially in the paragraphs 6.1.2.2.4. and 6.1.2.2.8., such as sieve plate columns, bubble cap plate columns, orderedly packed columns, randomly packed columns or sidestream takeoff columns or technical variants thereof.

The distillation can be carried out in a plurality of columns, as in 2 or 3 columns, but is advantageously carried out in a single column.

A preferred embodiment utilizes a mixture (V) comprising a mixture of an aminonitrile (I), especially 6-aminocapronitrile, and an amine (IV) to advantageously provide in step b) aminonitrile (I) as head product.

A preferred embodiment utilizes a mixture (V) comprising a mixture of an aminonitrile (I), especially 6-aminocapronitrile, diamine (II), especially hexamethylenediamine, and amine (IV) to advantageously provide in step b) aminonitrile (I), diamine (II) or mixtures thereof as head product.

A preferred embodiment utilizes a mixture (V) comprising a mixture of an aminonitrile (I), especially 6-aminocapronitrile, dinitrile (III), especially adiponitrile, and amine (IV) to advantageously provide in step b) aminonitrile (I), dinitrile (III) or mixtures thereof as head product.

According to the invention, a bottom product is obtained in step b).

According to the invention, aminonitrile (I), diamine (II), dinitrile (III) or mixtures thereof are distilled from this bottom product at a temperature which is lower than the temperature chosen in step b) under the autogenous pressure resulting at this temperature under distillation conditions.

It is advantageous to employ a temperature which is at least 1° C., preferably at least 5° C., especially at least 20° C., and most preferably at least 50° C. lower than that chosen in step b).

It is advantageous to employ a temperature which is not more than 200° C., preferably not more than 140° C. and especially not more than 130° C. lower than that chosen in step b).

The distillation may be carried out in customary apparatus as described for example in Kirk-Othmer, Encyclopedia of Chemical Technology, 3rd Ed., Vol. 7, John Wiley & Sons, New York, 1979, pages 870-881, preferably in Ullmann's Encyclopedia of Industrial Chemistry, 5th Ed., Vol. A25, VCH Verlagsgesellschaft mbH, Weinheim, p. 215-226, especially in the paragraphs 6.1.2.2.4. and 6.1.2.2.8., such as sieve plate columns, bubble cap plate columns, orderedly packed columns, randomly packed columns or sidestream takeoff columns or technical variants thereof.

The distillation can be carried out in a plurality of columns, as in 2 or 3 columns, but is advantageously carried out in a single column.

A preferred embodiment utilizes a mixture (V) comprising a mixture of an aminonitrile (I), especially 6-aminocapronitrile, and an amine (IV) to advantageously provide in step c) as product of value aminonitrile (I) as head product.

A preferred embodiment utilizes a mixture (V) comprising a mixture of an aminonitrile (I), especially 6-aminocapronitrile, diamine (II), especially hexamethylenediamine, and amine (IV) to advantageously provide in step c) as product of value aminonitrile (I), diamine (II) or mixtures thereof as head product.

A preferred embodiment utilizes a mixture (V) comprising a mixture of an aminonitrile (I), especially 6-aminocapronitrile, dinitrile (III), especially adiponitrile, and amine (IV) to advantageously provide in step c) as product of value aminonitrile (I), dinitrile (III) or mixtures thereof as head product.

A particularly preferred form of this preferred embodiment advantageously provides in step b) an aminonitrile (I), especially 6-aminocapronitrile, as head product and in step c) as product of value a dinitrile (III), especially adiponitrile, as head product.

A particularly preferred embodiment of this particularly preferred embodiment provides in a further distillation step between step b) and step c) for the removal of a head product which in a particularly advantageous form of this embodiment can be recycled into step a).

The head product obtained in step c) can advantageously be sent to the same use as the head product obtained in step b).

The head product obtained in step c) can in particular be recycled into step a) of the process according to the present invention.

Aminonitriles (I), diamines (II) and dinitriles (III) are precursors for the production of industrially important polyamides, such as nylon-6 or nylon-6,6.

Advantageously, the aminonitriles (I), preferably 6-aminocapronitrile, especially those obtained in step b), can be directly converted into polyamides, preferably in the case of 6-aminocapronitrile as aminonitrile (I) into nylon-6.

Advantageously, the dinitriles (III), preferably adiponitrile, especially those obtained in step b), can be directly converted into polyamides together with a diamine, preferably a diamine (II), especially hexamethylenediamine, preferably in the case of adiponitrile as dinitrile (III) into nylon-6,6.

Furthermore, aminonitriles (I), especially those obtained in step b), can be converted into lactams, preferably 6-aminocapronitrile to caprolactam. Such lactams are precursors for producing industrially important polyamides, such as nylon-6.

Furthermore, the head product obtained in step c) can be partly or wholly fed to a process for producing an aminonitrile, a diamine or mixtures thereof by partial or full hydrogenation of a dinitrile, especially in the case of 6-aminocapronitrile, hexamethylenediamine or mixtures thereof as head product in step c) into a process for partial or full hydrogenation of adiponitrile to obtain 6-aminocapronitrile, hexamethylenediamine or mixtures thereof and also, as the case may be, unconverted adiponitrile.

In a preferred embodiment, the bottom product obtained in step c) can be subjected to a further distillation, especially by means of a thin film evaporator, to obtain further head product as product of value.

EXAMPLES

Example 1

In accordance with step a), 110 g/h of a 6-ACN having a THA content of 420 weight ppm, based on the sum total of 6-ACN and THA, were pumped into a vessel in which, by addition of a 20% by weight aqueous solution of potassium phthalimide, a concentration of 130 weight ppm, based on the total weight of the mixture, was set. The temperature in this vessel was 170° C. coupled with an average residence time of 1.7 hours.

In accordance with step b), the mixture was pumped into a distillation apparatus having 35 theoretical separation stages where it was distilled at a head pressure of 4 kPa, a pot temperature of 144° C. and a reflux ratio of 1.7. The head product obtained was 106 g/h of a 6-ACN having a THA content of 37 weight ppm, based on the total weight of the mixture.

In accordance with step c), the bottom product was partially evaporated in a vessel at 90° C. and 0.1 kPa, the vapor, which contained 6-ACN as product of value, was condensed and recycled into the vessel as per step a). The bottom product obtained in step c) was discarded.

The yield of 6-ACN obtained in step b) was 97%, based on the 6-ACN used in step a).

We claim:

1. A process for reducing the level of an aliphatic monounsaturated amine (IV) in a mixture (V) containing an aliphatic aminonitrile (I) having from 4 to 12 carbon atoms or an aliphatic diamine (II) having from 4 to 12 carbon atoms or an aliphatic dinitrile (III) having from 4 to 12 carbon atoms or mixtures thereof as well as said amine (IV) by steps including
   a) reacting said mixture (V) with an anionic nucleophile (VI)
      which contains a nucleophilic atom selected from the group consisting of oxygen, nitrogen and sulfur,
      which is capable of taking up an H$^+$ ion to form an acid having a pK$_a$ value in the range from 7 to 11, as measured in water at 25° C., and
      which has a relative nucleophilicity, as measured in methyl perchlorate/methanol at 25° C.,
         in the range from 3.4 to 4.7 when said nucleophilic atom is oxygen,
         in the range from 4.5 to 5.8 when said nucleophilic atom is nitrogen, and
         in the range from 5.5 to 6.8 when said nucleophilic atom is sulfur,
      in an amount in the range from 0.01 to 10 mol per mole of said amine (IV) in said mixture (V) at a temperature in the range from 50 to 200° C. to obtain a mixture (VII),
   b) distilling said aminonitrile (I) or said diamine (II) or said dinitrile (III) or mixtures thereof from said mixture (VII) at a temperature in the range from 50 to 200° C. and at a pressure in the range from 0.1 to 100 kPa to obtain a bottom product (VIII), which comprises
   c) distilling an aminonitrile (I) or diamine (II) or dinitrile (III) or mixtures thereof from said bottom product (VIII) at a temperature which is lower than that chosen in step b), to obtain (I), (II) or (III) or mixtures thereof as a top product.

2. A process as claimed in claim 1, wherein said aminonitrile (I) is an aliphatic aminonitrile having from 4 to 12 carbon atoms and selected from the group consisting of 4-aminobutyronitrile, 5-aminovaleronitrile, 2-methyl-5-aminovaleronitrile, 6-aminocapronitrile and 12-aminododecanenitrile.

3. A process as claimed in claim 1, wherein said diamine (II) is an aliphatic diamine having from 4 to 12 carbon atoms and selected from the group consisting of 1,4-diaminobutane, 1,5-diaminopentane, 2-methyl-1,5-diaminopentane, 1,6-diaminohexane and 1,12-diaminododecane.

4. A process as claimed in claim 1, wherein said dinitrile (III) is an aliphatic dinitrile having from 4 to 12 carbon atoms and selected from the group consisting of 1,2-dinitriloethane, 1,3-dinitrilopropane, 1-methyl-1,3-dinitrilopropane, 1,4-dinitrilobutane and 1,10-dinitrilodecane.

5. A process as claimed in claim 1, wherein said amine (IV) is a compound selected from the group consisting of dihydropyrrole, tetrahydropyridine, 3-methyltetrahydropyridine, tetrahydroazepine, 2-aminoazepan, N-(2-azepano)1,6-diamino-hexane, N-(2-azepano)-6-aminocapronitrile and monounsaturated cyclododecylamines.

6. A process as claimed in claim 1, wherein said nucleophile (VI) is benzenesulfonamide anion.

7. A process as claimed in claim 1, wherein said nucleophile (VI) is phthalimide anion.

8. A process as claimed in claim 1, wherein said nucleophile (VI) is phenate.

9. A process as claimed in claim 1, wherein said nucleophile (VI) is a lactam anion of the general formula

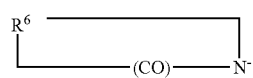

where R$^6$ is an alkylene radical having 3, 4, 5, 6, 7, 8, 9, 10 or 11 carbon atoms belonging to the ring system.

10. A process as claimed in claim 1, wherein said nucleophile (VI) is caprolactam anion.

11. A process as claimed in claim 1, wherein said anionic nucleophile (VI) is used together with a cation selected from the group consisting of lithium, sodium, potassium, magnesium and calcium.

12. A process as claimed in claim 1, wherein said mixture (V) is a mixture of said aminonitrile (I) and said amine (IV) to obtain said aminonitrile (I) in steps b) and c).

13. A process as claimed in claim 12, wherein said aminonitrile (I) obtained in step c) is recycled into step a).

14. A process as claimed in claim 1, wherein said mixture (V) is a mixture of said aminonitrile (I), said diamine (II) and said amine (IV) to obtain said aminonitrile (I), said diamine (II) or mixtures thereof in step b) and said aminonitrile (I), said diamine (II) or mixtures thereof in step c).

15. A process as claimed in claim 14, wherein said aminonitrile (I) or said diamine (II) obtained in step c) or mixtures thereof are recycled into step a).

16. A process as claimed in claim 1, wherein said mixture (V) is a mixture of said aminonitrile (I), said dinitrile (III) and said amine (IV) to obtain said aminonitrile (I), said dinitrile (III) or mixtures thereof in step b) and said aminonitrile (I), said dinitrile (III) or mixtures thereof in step c).

17. A process as claimed in claim 16, wherein said aminonitrile (I) or said dinitrile (III) obtained in step c) or mixtures thereof are recycled into step a).

18. A process as claimed in claim 16, wherein an aminonitrile (II) is obtained in step b) and a dinitrile (III) is obtained in step c).

19. A process comprising
i) conducting the process claimed in claim 1 to obtain the top product of step c), and
ii) feeding said top product in whole or in part into a process for producing an aminonitrile, a diamine or mixtures thereof by partial or full hydrogenation of a dinitrile.

20. A process comprising
i) conducting the process claimed in claim 1 to obtain 6-aminocapronitrile as the aminonitrile (I) obtained in step b), and
ii) converting this 6-aminocapronitrile directly into nylon-6.

21. A process comprising
i) conducting the process claimed in claim 1 to obtain 6-aminocapronitrile as the aminonitrile (I) obtained in step b), and
ii) converting this 6-aminocapronitrile to caprolactam.

22. A process comprising
i) conducting the process claimed in claim 1 to obtain adiponitrile as the dinitrile (III) obtained in step b), and
ii) converting this adiponitrile directly with hexamethylenediamine into nylon-6,6.

* * * * *